US006346500B1

(12) United States Patent
Pressman et al.

(10) Patent No.: US 6,346,500 B1
(45) Date of Patent: *Feb. 12, 2002

(54) CATALYST SYSTEM FOR PRODUCING AROMATIC CARBONATES

(75) Inventors: Eric James Pressman, East Greenbush; Grigorii Lev Soloveichik, Latham; Kirill Vladimirovich Shalyaev, Clifton Park; Bruce Fletcher Johnson, Scotia, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/578,400

(22) Filed: May 26, 2000

Related U.S. Application Data

(62) Division of application No. 09/383,425, filed on Aug. 27, 1999, now Pat. No. 6,114,564.

(51) Int. Cl.[7] .................... B01J 31/00; B01J 23/58; B01J 23/40; B01J 23/42
(52) U.S. Cl. .................... 502/159; 502/172; 502/224; 502/154; 502/328; 502/330; 502/339; 502/349; 502/326
(58) Field of Search ............... 502/172, 224, 502/328, 330, 339, 349, 154, 326, 159; 558/270–274

(56) References Cited

U.S. PATENT DOCUMENTS

| | | | |
|---|---|---|---|
| 4,187,242 A | | 2/1980 | Chalk |
| 4,201,721 A | | 5/1980 | Hallgren .................... 260/463 |
| 4,859,644 A | * | 8/1989 | Van Broekhoven et al. 502/154 |
| 5,231,210 A | | 7/1993 | Joyce et al. |
| 5,239,106 A | | 8/1993 | Shafer |
| 5,284,964 A | | 2/1994 | Pressman et al. |
| 5,373,083 A | | 12/1994 | King et al. |
| 5,380,907 A | | 1/1995 | Mizukami et al. |
| 5,399,734 A | | 3/1995 | King et al. |
| 5,498,789 A | | 3/1996 | Takagi et al. |
| 5,502,232 A | | 3/1996 | Buysch et al. |
| 5,543,547 A | * | 8/1996 | Iwane et al. |
| 5,625,091 A | * | 4/1997 | Buysch et al. ............... 558/274 |
| 5,726,340 A | | 3/1998 | Takagi et al. |
| 5,760,272 A | | 6/1998 | Pressman et al. |
| 5,767,303 A | * | 6/1998 | Minami et al. ............. 558/275 |
| 5,821,377 A | * | 10/1998 | Buysch et al. |
| 5,856,554 A | | 1/1999 | Buysch et al. |
| 6,001,768 A | * | 12/1999 | Buysch et al. ............... 502/330 |
| 6,114,563 A | * | 9/2000 | Spivack et al. ............. 502/326 |
| 6,143,914 A | * | 11/2000 | Spivack et al. ............. 558/274 |
| 6,160,155 A | * | 12/2000 | Spivack et al. ............. 502/167 |
| 6,172,254 B1 | * | 1/2001 | Pressman et al. ........... 558/274 |

FOREIGN PATENT DOCUMENTS

| | | |
|---|---|---|
| DE | 736325 | 3/1996 |
| JP | 10158221 | 6/1980 |
| JP | 06-211750 | 8/1994 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |

* cited by examiner

*Primary Examiner*—Mark L. Bell
*Assistant Examiner*—Patricia L. Hailey
(74) *Attorney, Agent, or Firm*—Ben P. Patel; Donald S. Igraham

(57) ABSTRACT

Hydroxyaromatic compounds such as phenol are carbonylated with oxygen and carbon monoxide in the presence of a catalyst system comprising a Group VIII metal having an atomic number of at least 44, preferably palladium; an alkali metal or alkaline earth metal halide, preferably sodium bromide; and at least one aliphatic polyether such as a polyethylene glycol dimethyl ether or a crown ether. The catalyst system also preferably contains a compound of another metal, preferably lead.

12 Claims, No Drawings

CATALYST SYSTEM FOR PRODUCING AROMATIC CARBONATES

CROSS REFERENCE TO RELATED APPLICATIONS

This application is a division of application Ser. No. 09/383,425, filed Aug. 27, 1999, now U.S. Pat. No. 6,114, 564, entitled "CATALYST COMPOSITION AND METHOD FOR PRODUCING DIARYL CARBONATES" and, accordingly, claims priority to and the benefit of the filing date of said application under 35 U.S.C. § 120. The parent application is incorporated herein by reference.

BACKGROUND OF THE INVENTION

This invention relates to the preparation of diary carbonates by carbonylation. More particularly, it relates to the improvement of diary carbonate yield in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is a heavy Group VIII metal; i.e., a Group VIII metal having an atomic number of at least 44, said metals consisting of ruthenium, rhodium, palladium, osmium, iridium and platinum, or a complex thereof.

The production of carbonates may be improved by including a metal-based cocatalyst along with the heavy Group VIII metal catalyst. Although the identity of suitable metal-based cocatalysts will depend on specific reaction conditions including the identity of reactants and other members of the catalyst package, some general guidance can be found in U.S. Pat. Nos. 4,187,242 and 4,201,721.

A further development in the carbonylation reaction, including the use of specific lead compounds as cocatalysts, is disclosed in U.S. Pat. No. 5,498,789. Also required according to that patent is the use of quaternary ammonium or phosphonium halides, as illustrated by tetra-n-butylammonium bromide, as part of the catalyst package. Compounds characterized as inert solvents, such as toluene, diethyl ether, diphenyl ether and acetonitrile, can also be present.

The commercial viability of the carbonylation reaction would be greatly increased if a less expensive compound could be substituted for the quaternary ammonium or phosphonium halide. Substitution of such compounds as sodium bromide, however, result in the isolation of the desired diaryl carbonate in low or insignificant yield.

It is of interest, therefore, to develop catalyst systems which include an inexpensive halide compound and which can efficiently produce diaryl carbonates. Some such systems are known. Reference is made, for example, to Japanese Kokai 10/316,627, which discloses the use of palladium and a lead or manganese compound in combination with a halide such as sodium bromide and with an amide or alkylurea. U.S. Pat. No. 5,726,340 and Japanese Kokai 9/278,716 disclose similar systems in which the lead is combined with another metal and in which inert solvents such as those mentioned hereinabove may be present. The development of other systems employing relatively inexpensive halides, however, remains desirable.

SUMMARY OF THE INVENTION

The present invention provides a method for preparing diaryl carbonates which includes a relatively inexpensive halide and a compound which maximizes the effectiveness of said halide. Also provided are catalyst compositions useful in such a method.

In one of its aspects, the invention provides a method for preparing a diaryl carbonate which comprises contacting at least one hydroxyaromatic compound with oxygen and carbon monoxide in the presence of an amount effective for carbonylation of at least one catalytic material comprising:

(A) a Group VIII metal having an atomic number of at least 44 or a compound thereof, (B) at least one alkali metal halide or alkaline earth metal halide, and (C) at least one polyether.

Another aspect of the invention is catalyst compositions comprising components A, B and C as described above, and any reaction products thereof.

DETAILED DESCRIPTION PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonate oligomers.

Other reagents in the method of this invention include oxygen and carbon monoxide, which can react with the phenol to form the desired diaryl carbonate. They may be employed in high purity form or diluted with another gas such as nitrogen, argon, carbon dioxide or hydrogen which has no negative effect on the reaction.

For the sake of brevity, the constituents of the catalyst system are defined as "components" irrespective of whether a reaction between said constituents occurs before or during the carbonylation reaction. Thus, the catalyst system may include said components and any reaction products thereof.

Component A of the catalyst system is one of the heavy Group VIII metals, preferably palladium, or a compound thereof. Thus, useful palladium materials include elemental palladium-containing entities such as palladium black, palladium/carbon, palladium/alumina and palladium/silica; palladium compounds such as palladium chloride, palladium bromide, palladium iodide, palladium sulfate, palladium nitrate, palladium acetate and palladium 2,4-pentanedionate; and palladium-containing complexes involving such compounds as carbon monoxide, amines, nitrites, phosphines and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate are generally most preferred. Palladium(II) acetylacetonate is also a suitable palladium source. Mixtures of the aforementioned palladium materials are also contemplated.

Component B is at least one alkali metal or alkaline earth metal halide, preferably a bromide such as lithium bromide, sodium bromide, potassium bromide, calcium bromide or magnesium bromide. Alkali metal bromides are especially preferred, with sodium bromide often being most preferred by reason of its particular suitability and relatively low cost.

Component C is at least one polyether; i.e., at least one compound containing two or more C—O—C linkages. The polyether is preferably free from hydroxy groups to maximize its desired activity and avoid competition with the hydroxyaromatic compound in the carbonylation reaction.

The polyether preferably contains two or more (O—C—C) units. The polyether may be "aliphatic" or mixed aliphatic-aromatic. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Suitable aliphatic polyethers include diethylene glycol dimethyl ether (hereinafter "diglyme"), triethylene glycol dimethyl ether (hereinafter "triglyme"), tetraethylene glycol dimethyl ether (hereinafter "tetraglyme"), polyethylene glycol dimethyl ether and crown ethers such as 15-crown-5 (1,4,7,10,13-pentaoxacyclopentadecane) and 18-crown-6 (1,4,7,10,13,16-hexaoxacyclooctadecane). Illustrative mixed aliphatic-aromatic polyethers are diethylene glycol diphenyl ether and benzo-18-crown-6.

In a highly preferred embodiment of the invention, there is also present in the catalyst system (D) at least one cocatalyst which is a compound of a metal other than a heavy Group VIII metal. This metal is preferably one which is soluble in the liquid phase under the reaction conditions. Numerous other metal compounds are known in the art to be active as carbonylation cocatalysts, and any compound having such activity may be used according to the present invention provided an improvement in diphenyl carbonate production, usually yield, is achieved thereby.

Illustrative cocatalytic metals include cerium, titanium, cobalt, copper, zinc, manganese, iron and lead, which may be used singly or in combination. For the purposes of this invention the preferred cocatalysts are those containing metals other than Group VIII metals; that is other than iron, cobalt and nickel. More preferred are compounds of lead, particularly when used alone or in combination with titanium and/or cerium. It should be noted, however, that component C is not effective to optimize diaryl carbonate formation for all possible permutations of component D; the combined effectiveness of the two for this purpose may be determined by simple experimentation.

Examples of lead compounds which may be employed are lead oxides such as PbO and $Pb_3O_4$; inorganic lead salts such as lead(II) nitrate; lead carboxylates such as lead(II) acetate and lead(II) propionate; lead alkoxides and aryloxides such as lead(II) methoxide and lead(II) phenoxide; and lead salts of β-diketones such as lead(II) 2,4-pentanedionate. Mixtures of the aforementioned lead compounds may also be employed. The preferred lead compounds are lead(II) oxide, lead(II) aryloxides and lead(II) 2,4-pentanedionate.

Examples of cerium compounds are cerium carboxylates such as cerium(II) acetate, and cerium salts of β-diketones such as cerium(III) 2,4-pentanedionate. Cerium(III) acetylacetonate and mixtures of the aforementioned cerium compounds may also be employed. The preferred cerium compounds are cerium 2,4-pentanedionates.

Examples of titanium compounds are inorganic titanium salts such as titanium(IV) bromide; titanium alkoxides and aryloxides such as titanium(IV) butoxide and titanium(IV) phenoxide; and titanium salts of β-diketones such as titanium(IV) oxide bis(2,4-pentanedionate). Titanium(IV) acetylacetonate and mixtures of the aforementioned titanium compounds may also be employed. The preferred titanium compounds are titanium(IV) alkoxides, aryloxides and 2,4-pentanedionates.

The preferred compounds of other metals are, for the most part, salts of β-diketones and especially 2,4-pentanedionates.

In addition to the aforementioned reactants and catalyst system, it is strongly preferred for a desiccant to be present in the reaction system. The preferred desiccants are non-reactive materials such as molecular sieves, as illustrated by 3-Ångstrom (hereinafter "3 Å") molecular sieves. They are usually isolated from the other reactants, as by presence in a basket mounted to a stirrer shaft or the like.

Component A is most often present in the amount of about 0.1–10,000 ppm by weight of the appropriate Group VIII metal (usually palladium), based on the total of hydroxyaromatic compound and component C, and component B in the amount of about 1–2,000 mol per mole of the Group VIII metal of component A. Component D, when employed, is generally present in the amount of about 1–200 mole of total metal per equivalent of the Group VIII metal of component A.

The role of component C in the composition and method of the invention is believed to be to increase the degree of dissociation and ionization of the halide anion of component B, perhaps by forming a complex with the cationic portion of said component, although the invention is in no way dependent on this or any other theory of operation. The amount of component C employed will be an amount effective to optimize diaryl carbonate formation, in general by increasing the yield of the desired diaryl carbonate as evidenced, for example, by an increase in "turnover number"; i.e., the number of moles of diary carbonate formed per gram-atom of palladium present. This amount is most often about 1–60% by volume based on the total of hydroxyaromatic compound and component C.

The amount of component C will, however, typically depend to some extent on the complexing ability of the organic compound employed. Crown ethers, for example, have a very high complexing tendency with metal cations. For example, 15-crown-5 complexes efficiently with sodium and 18-crown-6 with potassium. Such compounds may be used in amounts as low as an equimolar amount based on component B. Other compounds useful as component C, such as straight chain polyethers (e.g., diglyme), may be optimally effective at much higher levels, often up to 1–60% by volume based on total polyether and phenol; near the higher end of this range, they can also function as cosolvents. The preferred proportion of any specific material used as component C can be determined by simple experimentation.

The method of the invention is preferably conducted in a reactor in which the hydroxyaromatic compound and catalyst system are charged under pressure of carbon monoxide and oxygen and heated. The reaction pressure is most often within the range of about 1–500 and preferably about 1–150 atm. Gas is usually supplied in proportions of about 1–50 mole percent oxygen with the balance being carbon monoxide, and in any event, outside the explosion range for safety reasons. The gases may be introduced separately or as a mixture. Reaction temperatures in the range of about 60–150° C. are typical. In order for the reaction to be as rapid as possible, it is preferred to substantially maintain the total gas pressure and partial pressure of carbon monoxide and oxygen, as described, for example, in U.S. Pat. No. 5,399,734, until conversion of the hydroxyaromatic compound is complete.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 5,239,106 and 5,312,955.

The method of the invention is illustrated by the following examples. Minor variations in reagent amounts from one example to another are not believed significant from the standpoint of yield. Unless otherwise noted, all equivalents are molar equivalents relative to palladium.

EXAMPLES 1–3

A constant composition gas flow reactor system, as disclosed in the aforementioned U.S. Pat. No. 5,399,734, was charged in each example with 61.1 g (649 mmol) of phenol, 4.9 mg (0.016 mmol) of palladium(II) 2,4-pentanedionate (28 ppm of palladium based on phenol), 205 mg (0.92 mmol, 58 eq.) of lead(II) oxide, 650 equivalents of sodium bromide or lithium bromide and various proportions of 15-crown-5 or diglyme. Molecular sieves, 38 g, were placed in a perforated polytetrafluoroethylene basket mounted to the stir shaft of the reactor.

The reactor was sealed, pressurized to 89.8 atm with a mixture of 9.1 mole percent oxygen and 90.9 mole percent carbon monoxide and stirred as its temperature was increased to 100° C. over 10 minutes. Further oxygen-carbon monoxide mixture was introduced at a flow rate of 330 ml/min and a pressure of about 88.5 atm. Gas flow was continued for 2.5 hours, during which the reaction mixture was analyzed every 30 minutes by high pressure liquid chromatography.

The results are given in Table I, in comparison with two controls: Control 1 in which the bromide source was tetraethylammonium bromide (TEAB), and Control 2 in which sodium bromide was employed without the use of component C. Turnover numbers are those observed at the point of highest diphenyl carbonate content of each reaction mixture, as shown by analysis.

TABLE I

| Example | Component B | Component C identity | Component C vol. % | Turnover number |
|---|---|---|---|---|
| 1 | NaBr | 15-Crown-5 | 3.5 | 5,455 |
| 2 | NaBr | Diglyme | 54 | 1,655 |
| 3 | LiBr | Diglyme | 10.8 | 2,212 |
| Control 1 | TEAB | — | — | 5,587 |
| Control 2 | NaBr | — | — | 626 |

It can be seen that the proportion of diphenyl carbonate produced, as shown by turnover number, is substantially higher for Examples 1–3 than for Control 2 in which component C was not employed. In Example 1, the turnover number was comparable to that of Control 1 employing the considerably more expensive quaternary ammonium bromide.

EXAMPLE 4

The procedure of Examples 1–3 was repeated except that the molecular sieves were omitted, the polyether was tetraglyme at 7.9% by volume and the levels of palladium, lead and sodium bromide were 17 ppm, 56 gram-atoms and 357 equivalents, respectively. The turnover number was 2,857.

EXAMPLE 5

The procedure of Examples 1–3 was repeated except that the polyether was tetraglyme at 26% by volume, the bromide was potassium bromide at a level of 775 equivalents and the level of lead was 56 gram-atoms. The turnover number was 4,128.

EXAMPLES 6–8

A Parr 450-ml Hastelloy reactor was charged at room temperature with phenol (80–85 g), Pd(II) 2,4-pentanedionate (component A) at various levels, 56 eq. lead(II) oxide, 4 eq. titanium(IV) oxide 2,4-pentanedionate, polyether (4.5–8.5% by volume) and sodium bromide at various levels. Molecular sieves (3 Å, 30 g) were placed in a perforated polytetrafluoroethylene basket mounted to the stir shaft of the reactor. The reactor was sealed and pressurized to 108.8 atm with a mixture of 9% (by volume) oxygen and 91% carbon monoxide. The reactor was heated under stirring (1600 rpm) to 100° C. over 10 min and stirred over 1.5 hours, with periodic sampling. Tetraglyme or a polyethylene glycol dimethyl ether having a molecular weight of about 250 (designated "PEGDME") was employed as component C. The results are given in Table II.

TABLE II

| Example | 6 | 7 | 8 |
|---|---|---|---|
| Component A, ppm | 17 | 13 | 14 |
| Component B, eq | 230 | 448 | 454 |
| Component C vol. % | Tetraglyme (8.45) | Tetraglyme (7.15) | PEGDME (4.77) |
| Turnover number | 4,620 | 6,.145 | 6,784 |

EXAMPLES 9–16

Carbonylation experiments were conducted in small vials, employing palladium(II) 2,4-pentanedionate (24 ppm of palladium based on phenol and cosolvent), sodium bromide and various ethers. Various cocatalyst compounds which included lead(II) oxide, titanium(IV) oxide bis(2,4-pentanedionate), cerium(III) 2,4-pentanedionate and copper (II) 2,4-pentanedionate, employed alone or in combination, were employed as component D. Each vial was capped with snap caps having a slit with a polytetrafluoroethylene septum and the vials were placed in an autoclave which was pressurized to 81.6 atm with a mixture of 91.7 mole percent carbon monoxide and 8.3 mole percent oxygen and heated at 100° C. for 3 hours. The contents of the vials were analyzed for diphenyl carbonate by vapor phase chromatography.

The results are given in Table III as averages of duplicate or triplicate runs. Cocatalyst proportions are in equivalents per equivalent of palladium, and ether proportions are in percent by volume based on phenol. Controls contain an equivalent volume of phenol instead of component C.

TABLE III

| Example | Component B, eq | Component C (vol. %) | Component D metal (eq) | Turnover number | Control turnover number |
|---|---|---|---|---|---|
| 9 | 445 | PEGDME (15) | Pb (48) | 2,804 | 215 |
| 10 | 270 | Triglyme (35) | Pb (48) | 1,186 | 152 |
| 11 | 111 | PEGDME (15) | Pb (47), Ti (10) | 1,481 | 162 |
| 12 | 270 | Triglyme (35) | Pb (47), TI (10) | 1,249 | 472 |
| 13 | 106 | Diglyme (15) | Pb (47), Ce (6) | 1,065 | 183 |
| 14 | 100 | PEGDME (15) | Pb (47), Ce (6) | 1,098 | 183 |
| 15 | 111 | PEGDME (15) | Cu (20) | 941 | 218 |
| 16 | 111 | PEGDME (15) | Cu (20), Ti (10) | 1,233 | 160 |

What is claimed is:

1. A catalyst composition comprising the following:
   (A) a Group VIII metal having an atomic number of at least 44 or a compound thereof,
   (B) at least one alkali metal halide or alkaline earth metal halide, and
   (C) at least one polyether, wherein the polyether of component C increases the degree of dissociation and ionization of the halide anion of component B.

2. A composition according to claim 1 further comprising (D) at least one cocatalyst which is a compound of a metal which is not a Group VIII metal having an atomic number of at least 44.

3. A composition according to claim 2 wherein component C is an aliphatic polyether free from hydroxy groups.

4. A composition according to claim 2 wherein component A is palladium(II) acetate or palladium(II) 2,4-pentanedionate.

5. A composition according to claim 2 wherein component D is lead(II) oxide, a lead(II) aryloxide or lead(II) 2,4-pentanedionate.

6. A composition according to claim 2 wherein component D is at least one member selected from the group consisting of lead(II) oxide, a lead(II) aryloxide, and lead(II) 2,4-pentanedionate, wherein the lead compound is combined with at least one member selected from the group consisting of titanium(IV) alkoxide, titanium(IV) aryloxide, and titanium(IV) 2,4-pentanedionate.

7. A composition according to claim 2 wherein component D is at least one member selected from the group consisting of lead(II) oxide, a lead(II) aryloxide, and lead(II) 2,4-pentanedionate, wherein the lead compound is combined with a cerium 2,4-pentanedionate.

8. A composition according to claim 2 wherein component B is sodium bromide.

9. A composition according to claim 2 wherein component C is selected from the group consisting of diethylene glycol dimethyl ether, triethylene glycol dimethyl ether, tetraethylene glycol dimethyl ether, polyethylene glycol dimethyl ether, 15-crown-5 and 1 8-crown-6.

10. A composition according to claim 9 wherein component C is diethylene glycol dimethyl ether, triethylene glycol dimethyl ether or tetraethylene glycol dimethyl ether.

11. A catalyst composition comprising the following:
    (A) a Group VIII metal having an atomic number of at least 44 or a compound thereof,
    (B) at least one alkali metal halide or alkaline earth metal halide,
    (C) at least one polyether, and
    (D) copper(II) bis(2,4-pentanedionate), wherein the polyether of component C increases the degree of dissociation and ionization of the halide anion of component B.

12. A catalyst composition comprising:
    (A) palladium or a compound thereof,
    (B) sodium bromide,
    (C) at least one aliphatic polyether free from hydroxy groups, and
    (D) at least one lead compound.

* * * * *